US007686791B2

(12) United States Patent
Ramage et al.

(10) Patent No.: US 7,686,791 B2
(45) Date of Patent: Mar. 30, 2010

(54) EMESIS CONTAINER

(76) Inventors: Richard F Ramage, 560 Mystic Way, Laguna Beach, CA (US) 92651; Anthony F Ramage, 2526 Hall Canyon Rd., Ventura, CA (US) 93001; Phillip M Leopold, 118 Stone Marsh, North Barrington, IL (US) 60010; Joel C Anderson, 616 W. Fulton, Apt 207, Chicago, IL (US) 60661

( * ) Notice: Subject to any disclaimer, the term of this patent is extended or adjusted under 35 U.S.C. 154(b) by 0 days.

(21) Appl. No.: 11/714,949

(22) Filed: Mar. 7, 2007

(65) Prior Publication Data

US 2008/0221535 A1 Sep. 11, 2008

(51) Int. Cl.

| | |
|---|---|
| ***A61M 1/00*** | (2006.01) |
| *B65D 5/36* | (2006.01) |
| *B65D 5/46* | (2006.01) |
| *B65D 3/00* | (2006.01) |
| *B65D 25/54* | (2006.01) |
| *B65D 25/56* | (2006.01) |
| *B65D 33/10* | (2006.01) |
| *B65D 33/14* | (2006.01) |
| *B65D 33/00* | (2006.01) |
| *B65D 33/04* | (2006.01) |
| *B65D 30/10* | (2006.01) |

(52) U.S. Cl. .................. 604/317; 604/327; 229/117.03; 229/117.09; 229/117.21; 229/117.23; 229/117.24; 229/117.27; 229/117.3; 229/117.34; 229/162.1; 229/162.2; 383/8; 383/24; 383/33; 383/106; 383/123

(58) Field of Classification Search ................. 604/317, 604/318, 327, 77, 78, 303; 383/6, 7, 8, 22, 383/106, 108, 113, 121, 123, 125, 126, 903; 229/117.18, 117.28, 162.1, 0.2, 5.81
See application file for complete search history.

(56) References Cited

U.S. PATENT DOCUMENTS 1,588,094 A * 6/1926 Lee ............................ 224/608
1,592,283 A * 7/1926 Mckenzie ........................ 2/48
1,597,556 A 8/1926 Townsend
1,692,951 A 11/1928 Pinckney (Continued)

FOREIGN PATENT DOCUMENTS

WO WO 98/43593 10/1998

OTHER PUBLICATIONS

Online encyclopedia, "Stress concentration." Accessed Jan. 8, 2008. http://en.wikipedia.org/wiki/Stress_riser.*

(Continued)

*Primary Examiner*—Leslie R. Deak
*Assistant Examiner*—Adam Marcetich
(74) *Attorney, Agent, or Firm*—Ryan, Kromholz & Manion, S.C.

(57) ABSTRACT

A collapsible, hands-free emesis container is provided with improved portability, deployment and emesis reception characteristics. The container includes a receptacle for receiving emesis, a chute for directing emesis and a retainer to maintain desired positioning of the container about a support structure, which may be the neck of an impaired patient. The container may be provided in a package having size characteristics for easy storage and access by emergency medical service personnel.

23 Claims, 7 Drawing Sheets

U.S. PATENT DOCUMENTS

| | | | | | |
|---|---|---|---|---|---|
| 1,939,797 | A | | 12/1933 | Swift | |
| 2,323,287 | A | | 7/1943 | Amberg | |
| 2,374,153 | A | * | 4/1945 | Holtvoigt | 217/122 |
| 2,697,222 | A | | 12/1954 | Reid | |
| 2,943,660 | A | | 7/1960 | Seeger | |
| 2,948,936 | A | * | 8/1960 | Mitchell | 24/66.11 |
| 3,032,773 | A | * | 5/1962 | Piazze | 2/48 |
| D206,425 | S | | 12/1966 | Faughnder | |
| 3,578,236 | A | | 5/1971 | Masayuki | |
| 3,693,192 | A | | 9/1972 | Knotts | |
| 3,797,734 | A | | 3/1974 | Fleury et al. | |
| 3,920,179 | A | * | 11/1975 | Hall | 604/317 |
| 3,945,048 | A | | 3/1976 | Shearer | |
| 4,169,472 | A | * | 10/1979 | Morris | 128/854 |
| 4,182,478 | A | | 1/1980 | Etes | |
| 4,233,688 | A | | 11/1980 | Hjerl | |
| 4,301,925 | A | * | 11/1981 | Bogart | 383/203 |
| 4,379,519 | A | * | 4/1983 | Sherwood | 383/33 |
| 4,598,458 | A | | 7/1986 | McAllester | |
| 4,610,039 | A | | 9/1986 | Stern | |
| 4,660,226 | A | | 4/1987 | Quilling et al. | |
| 4,838,327 | A | * | 6/1989 | Ambler et al. | 141/114 |
| 4,946,094 | A | * | 8/1990 | Stang | 224/270 |
| 4,990,145 | A | | 2/1991 | Fleury | |
| 5,056,932 | A | * | 10/1991 | Young | 383/36 |
| 5,062,558 | A | * | 11/1991 | Stang | 224/270 |
| 5,067,821 | A | | 11/1991 | Young | |
| 5,112,322 | A | * | 5/1992 | Hathaway | 604/317 |
| 5,133,085 | A | * | 7/1992 | de Pasquale Amicarelli et al. | 2/69.5 |
| 5,354,132 | A | | 10/1994 | Young et al. | |
| 5,356,398 | A | | 10/1994 | Willis | |
| 5,368,583 | A | * | 11/1994 | Fleury | 604/318 |
| 5,425,468 | A | | 6/1995 | Birkel et al. | |
| 5,599,332 | A | | 2/1997 | Cashel | |
| 5,647,670 | A | * | 7/1997 | Iscovich | 383/33 |
| 5,875,490 | A | * | 3/1999 | Woodard et al. | 2/49.1 |
| 5,971,969 | A | | 10/1999 | Cashel | |
| 6,016,772 | A | * | 1/2000 | Noyes | 119/863 |
| 6,024,094 | A | | 2/2000 | Utecht | |
| 6,070,277 | A | | 6/2000 | Thomas | |
| 6,128,780 | A | | 10/2000 | Reinhart et al. | |
| 6,273,608 | B1 | | 8/2001 | Ward, Jr. et al. | |
| 6,554,810 | B1 | | 4/2003 | Wilk et al. | |
| 6,568,587 | B1 | * | 5/2003 | Yamada et al. | 229/162.1 |
| 6,589,220 | B2 | | 7/2003 | Taylor | |
| 6,602,230 | B1 | * | 8/2003 | Fisher et al. | 604/317 |
| 6,789,265 | B1 | | 9/2004 | Vonrinteln | |
| 6,826,780 | B1 | * | 12/2004 | Romesburg | 2/49.2 |
| 6,874,936 | B2 | | 4/2005 | Gillis et al. | |
| 6,991,373 | B2 | | 1/2006 | Carr et al. | |
| 7,029,463 | B1 | | 4/2006 | Estudillo | |
| 7,041,042 | B2 | | 5/2006 | Chertkow et al. | |
| 2001/0054191 | A1 | * | 12/2001 | Frye | 2/49.2 |
| 2002/0095709 | A1 | * | 7/2002 | Fujikawa et al. | 2/51 |
| 2003/0009140 | A1 | | 1/2003 | Taylor | |
| 2004/0001653 | A1 | | 1/2004 | Coval Carr et al. | |
| 2005/0261644 | A1 | * | 11/2005 | Fields | 604/317 |
| 2007/0088299 | A1 | | 4/2007 | Ayre | |

OTHER PUBLICATIONS http://www.hcl.intl.com/mail/more.asp?fmmore=7631 Fall 2006.

http://www.hcl.intl.com/mail/more.asp?fmmore=11178 Sep. 22, 2006.

Web page, Em-Assist, date unknown. https://www.fhmed.com/cgi-bin/smiva?fhmed/Merchant2/merchant.mv+Screen=CTGY&Store_Code=FM&Category_Code=Em-Assist Also, copy of product packaging—Em-Essist, same item, date unknown.

* cited by examiner

EMESIS CONTAINER

BACKGROUND OF THE INVENTION

The present invention relates generally to bodily fluid containment devices, and more specifically to a hands-free emesis container.

Emergency medical service (EMS) workers frequently encounter situations where a patient is unconscious, semi-conscious, altered, weak or otherwise impaired. The workers must act quickly to evaluate and stabilize the patient, set up IVs, prepare the patient for transport, communicate with hospital emergency staff, administer medications, and monitor and transport the patient to the hospital. These situations frequently involve patients who are vomiting or are on the verge of vomiting.

Emesis, or regurgitated contents of the stomach, is a medical treatment reality. Emesis further complicates emergency medical situations by distracting EMS workers from other important tasks. The workers suddenly find themselves juggling and holding traditional emesis basins or bags near the patient's face while simultaneously performing other lifesaving tasks, thereby reducing the multi-tasking efficiency of EMS workers. Despite a caregiver's best efforts, traditional emesis devices do not prevent patients from vomiting all over themselves while EMS workers are attending to other tasks.

In general, emesis containers are known in the art. These devices have several drawbacks, however. Most of the prior devices are not collapsible. An emesis container that is not collapsible may be suitable for some environments, but in an emergency medical situation, such configuration is inconvenient. If a collapsible container was provided in the past, it consisted of multiple pieces that required assembly prior to use. Such assembly simply subtracts precious seconds from attending to other medical needs in an emergency situation.

Additionally, prior devices did not address adequately the needs of a patient that is largely impaired. Most traditional emesis containers required, as previously noted, that the patient or caregiver support the container near the patient's mouth. While some devices offered supporting mechanisms, such as neckstraps, a minor patient head movement may remove the container from the flow path of the emesis, thereby allowing containment of only some of the fluid.

Therefore, the field of emergency medicine would benefit from a hands-free, collapsible emesis container with improved deployment and emesis reception characteristics.

SUMMARY OF THE INVENTION

The present invention provides a hands-free, collapsible emesis container with improved deployment and emesis reception characteristics.

The container is comprised generally of a receptacle, a chute, and a retainer. The receptacle is preferably a liquid impervious material that may enable inspection of contents and may have volume demarcations thereon. The receptacle has an open end having a perimeter and a closed end. The chute is preferably a fluid impervious material having a back panel, with a front surface and back surface, of substantial surface area and side panels extending from the bottom panel front surface. The junction of the bottom panel and the side panel provide a fluid trough. Extending from the chute and at least partially around the bag open end perimeter are support tabs. The support tabs provide added structural integrity for maintaining the open end of the receptacle in a wide open position.

Although emesis always complicates an emergency situation, the availability of a hands-free emesis container will help considerably. Such availability is provided by a preferred method of packaging the container, which allows the emesis container to be carried easily by emergency personnel in their starter boxes, fanny packs, shirt pockets or glove holsters. Quickly attaching a hands-free emesis container to a patient will enable EMS workers to multitask more efficiently without being distracted by holding traditional emesis containers near the face of an impaired patient. Attachment of the device to a patient is enabled by the retainer, which is preferably adapted to be situated around the patient's head or neck. With the aid of a chute having an increased surface area and curbed side sections, EMS workers can attend to other life-saving tasks, even when the patient is incapable of holding a conventional emesis container or substitute device, such as a trash can or bag.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
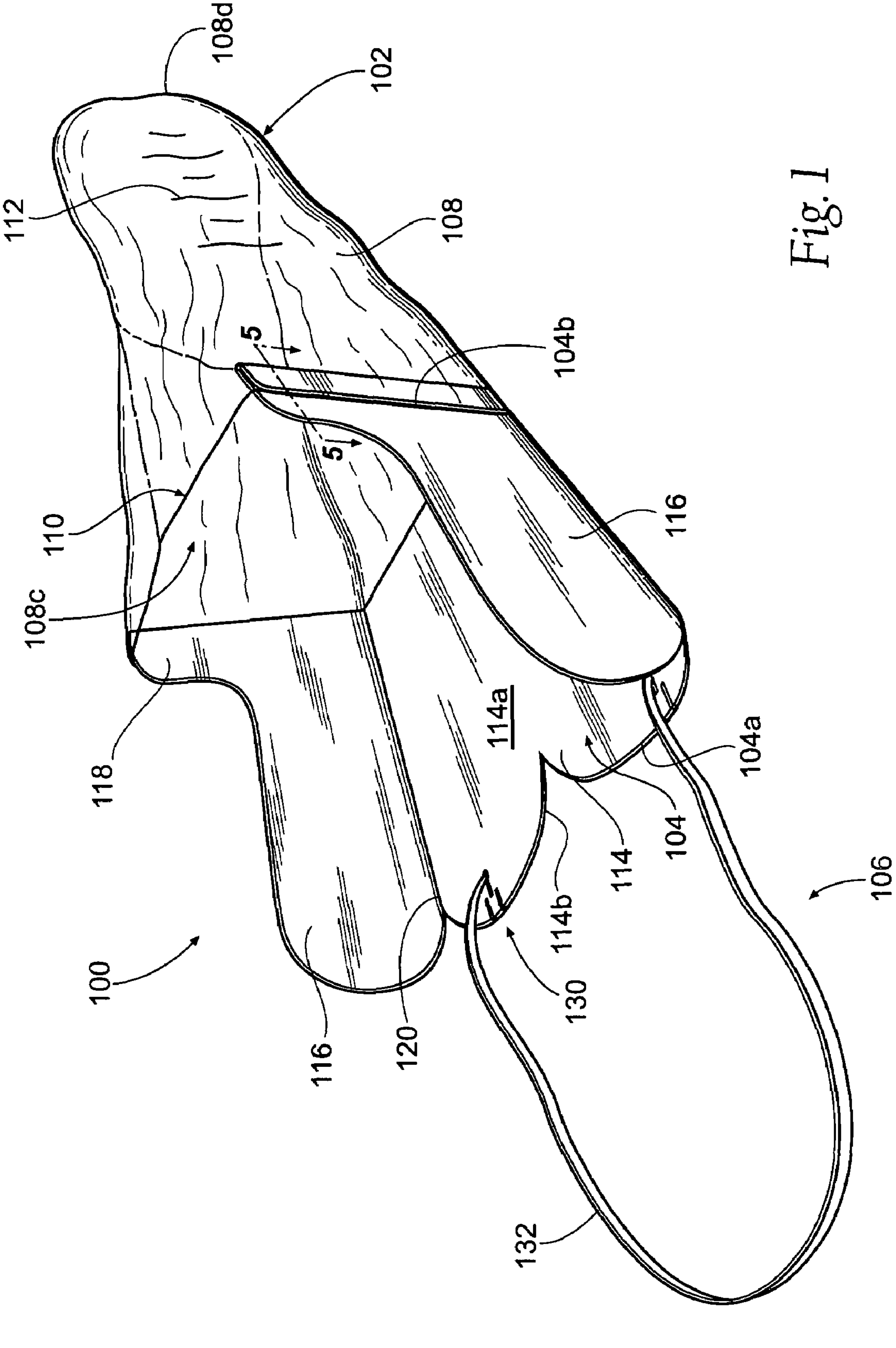
FIG. 1 is a perspective view of an embodiment of an emesis container according to the present invention.

Referring to FIG. 1, an embodiment of an improved emesis container 100 is shown. The container 100 includes a receptacle 102, a chute 104, and a retainer 106.

Figure 2:
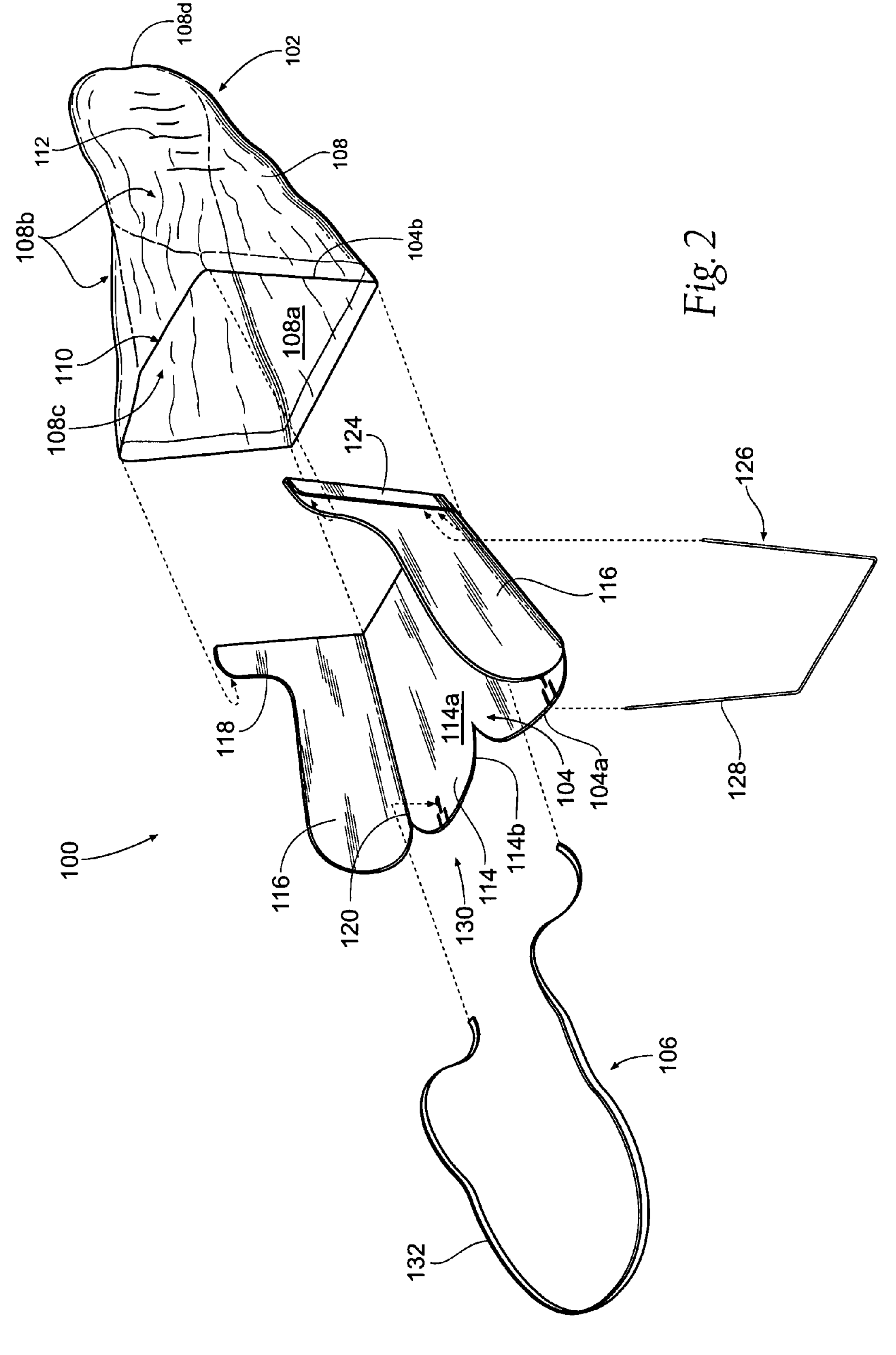
FIG. 2 is a perspective exploded view of the embodiment of FIG. 1.

With reference also to FIG. 2 the receptacle 102 is preferably in the form of a bag 108 having a back portion 108*a* and two side portions 108*b* extending between an open end 108*c* and a closed end 108*d*. The open end 108*c* of the bag 108 has a perimeter 110. The bag 108 is preferably formed from a flexible, liquid impervious material, such as polyethylene.

While it should be understood that the receptacle 102 may be of any desirable size, a preferred bag has a capacity of at least 1200 milliliters of liquid. Furthermore, to aid in monitoring a patient's condition, the receptacle 102 may be provided with volume demarcations 112, which indicate the amount of liquid contained in the receptacle 102. In addition, the receptacle 102 may be formed of a material that is transparent or translucent to allow quick visual inspection of the container contents.

Figure 3B:
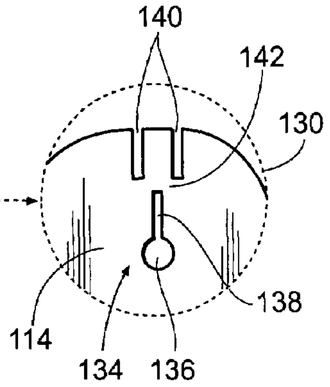
FIG. 3B is a close-up view of a retainer site on the chute of FIG. 3A.
Figure 3A:
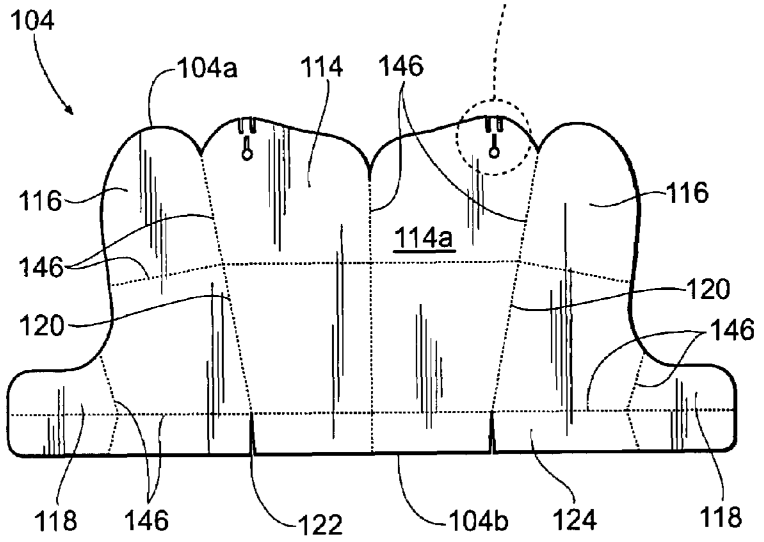
FIG. 3A is a front elevation view of an embodiment of an emesis chute according to the present invention.
Figure 3C:
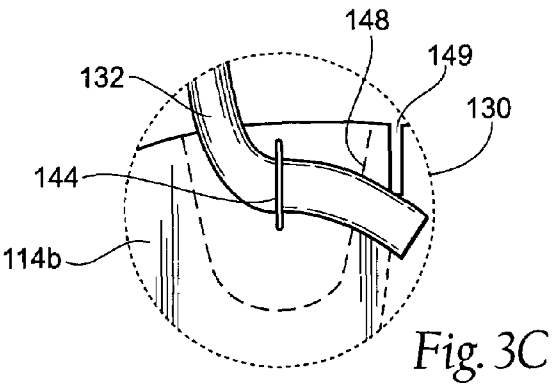
FIG. 3C is a close-up of an alternate retainer site.

Coupled to the receptacle 102 is the chute 104. Referring more specifically to FIGS. 3A-C, in addition to FIGS. 1 and 2, the chute 104 preferably comprises an entrance end 104*a* and an exit end 104*b*, with a back panel 114 and side panels 116 extending therebetween. The back panel 114 has a front surface 114*a* and a back surface 114*b*. The back panel front surface 114*a* is generally the receiving surface for emesis and, therefore, preferably has sufficient surface area to help collect the emesis. The preferred surface area comprises at least forty square inches. The side panels 116 preferably extend away from the back panel front surface 114*a*, perpendicularly or obliquely, along a panel junction 120, which may be provided as a score or crease 146. The side panels 116 may be formed integrally with the back panel 114 or attached thereto. To enable one method of assembly, the exit end 104*b* of the chute 104 is preferably formed with notches 122 proximate the panel junction 120. The chute 104 preferably includes an attachment margin 124 including and extending from the exit end 104*b* towards the entrance end 104*a*. The chute 104 preferably extends around less than the entire bag open end perimeter 110. The open end perimeter 110 preferably encompasses an area of at least thirty square inches. The chute 104 may be comprised of a material that is more rigid than the material comprising the receptacle 102. The added rigidity helps to maintain the receptacle 102 in a wide open configuration when the device 100 is in use.

To provide reinforcement that helps to maintain the receptacle 102 in an open configuration when the container 100 is in use, support tabs 118 are coupled to or formed integrally with the chute 104. While it is preferred that the chute 104 not extend around the entire bag open end perimeter 110 (see FIG. 1), the support tabs 118 may do so (not shown). To add further support to a coupling of the receptacle 102 and the chute 104, a reinforcement member 126 may be used. While various reinforcement members 126 will occur to those having skill in the art, the preferred reinforcement member 126 is a plastically deformable member such as a metal wire 128 or flat metal strip (not shown). The plastic deformability of the wire 128 aids in positioning and maintaining the open end 108*a* of the receptacle 102 in a desirable wide open configuration. Furthermore, the chute 104 may be provided with score lines 146, including the panel junctions 120, to aid in manufacturing, folding and packaging the container 100. A plurality of reinforcement members could also be used, such as foldable L- or U-shaped channel reinforcement structures (not shown) arranged over and supporting predetermined score lines 146.

To provide hands-free emesis collection by the container 100, a retainer 106 is provided, which is coupled to the chute 104 at retainer sites 130. While the retainer 106 may take many forms, the retainer 106 preferably comprises a flat strap 132. As seen in FIGS. 3A and 3B, a first preferred retainer site 130 comprises an aperture 134 having a hole 136 and a slot 138, and notches 140 cooperating with the aperture 134 to create a stress riser 142. The shape of the hole 136 is not specific or limiting. Rather, the hole 136 provides an area of less frictional resistance—than the slot 138—between the chute 104 and the retainer 106. A second preferred retainer site 130 is provided in FIG. 3C. In this embodiment, the retainer 106 is a flat strap 132 held in slidable, frictional contact with the chute 104 by a staple 144. In this embodiment, the frictional resistance between the chute 104 and the retainer 106 is kept relatively constant. With an appropriate choice of retainer 106, however, such as a strap 132 having elastic properties, when the retainer 106 is stretched, the friction lessens, enabling adjustment of the retainer 106 in the direction of the application of the stretching force. About the staple 144, perforations 148 may be provided, thereby creating at least one stress riser to enable tearing or removal of a portion the chute material for a quick disconnect of the device 100 from a patient or other support. Further, if a staple 144 is used to maintain the strap 132 in contact with the chute 104, the ends of the strap 132 may be provided with an inelastic portion or obstruction, such as a knot or aglet (not shown), that would prevent slippage through the staple 144, thereby preventing accidental removal of the strap 132 from the retainer site 122. In addition, an additional friction fit slot 149 may be provided in addition to the staple 144 to further reinforce the coupling of the retainer 106 to the chute 104.

Turning now to FIGS. 4A-D, a preferred method of assembling an embodiment of an emesis container according to the present invention includes forming the receptacle 102, the chute 104 and the retainer 106, and then coupling the components together. The receptacle 102 is formed from raw materials. For instance, where the receptacle 102 is a bag 108, polyethylene sheet material may be used. The chute 104 may be formed from a material suitable for liquid exposure over a determinable time. For example, the chute 104 may comprise a paperboard material having at least one side coated with a liquid impervious wax or plastic coating. The retainer 106 may be a simple flat strap portion cut from a spool of material.

Figure 4A:
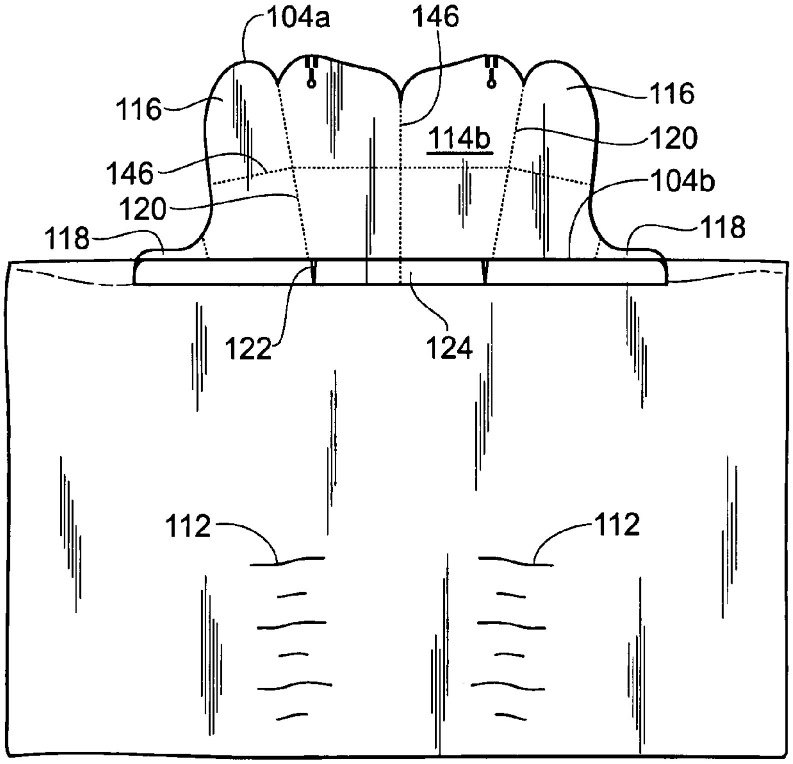
FIG. 4A is a front elevation view of a first assembly step in a first process for assembling the emesis container of FIG. 1.

After the receptacle raw material is selected and the chute 104 is formed, the coupling of the bag 108 to the chute 104 is achieved preferably through the use of a thermal bonding process including a thermal press or crimp. While the bag material could simply be thermally pressed to the chute attachment margin 124 or other attachment points, it is preferred that the attachment margin 124 be folded towards the chute back panel back surface 114*b* (as shown) or folded towards the chute back panel front surface 114*a* (not shown). Into the fold, the material to comprise the bag 108 may be inserted and then heat bonded to both the chute attachment margin 124 and the chute back surface 104*b*. The sheet material is then folded over the attachment margin 124, as is shown in FIG. 4A.

Figure 4B:
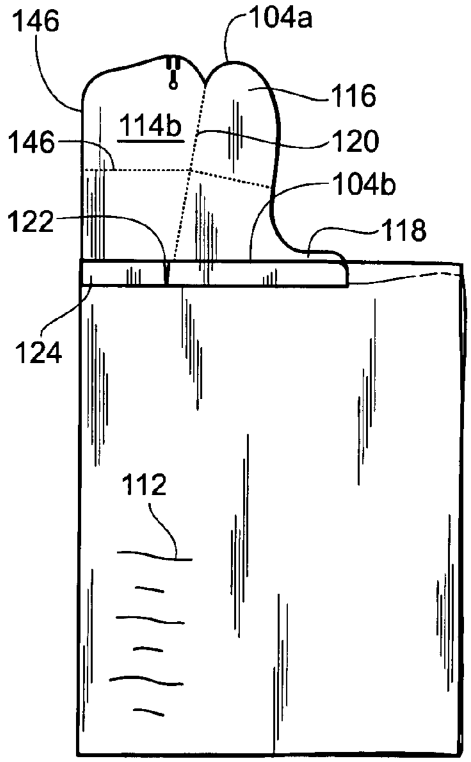
FIG. 4B is a front elevation view of a second assembly step in the first process for assembling the emesis container of FIG. 1.
Figure 4C:
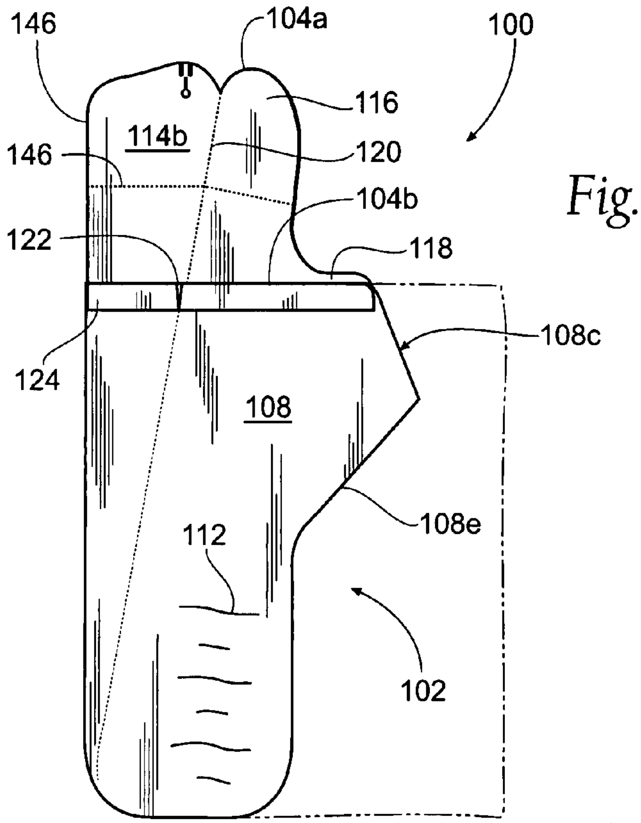
FIG. 4C is a front elevation view of a third assembly step in the first process for assembling the emesis container of FIG. 1.
Figure 4D:
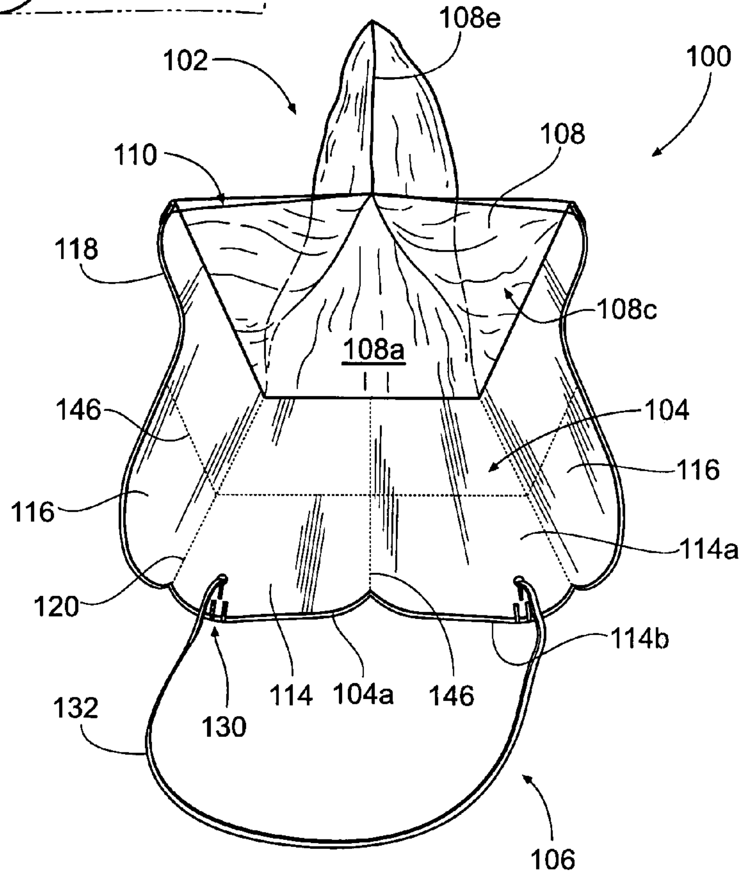
FIG. 4D is a top perspective view of the embodiment of FIG. 1.
Figure 5:
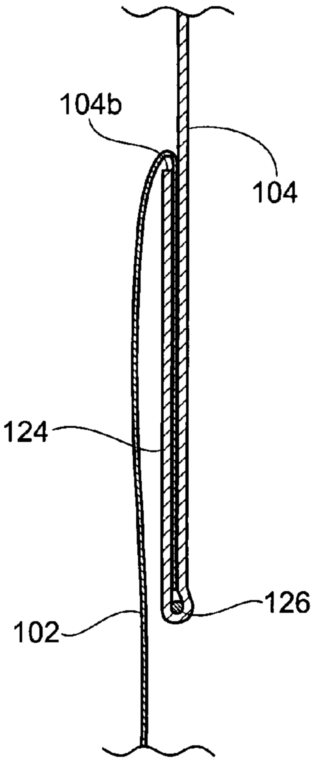
FIG. 5 is a partial cross-section view taken along line 5-5 in FIG. 1.

After the bag material has been heat sealed to the chute 104, the chute 104 may be folded along a medial score 146, thereby causing the sheet material to fold too, as seen in FIG. 4B. A formed joint can be seen in FIG. 5. A desired shape of the bag 108 may be obtained by using a heat sealer, such as an L-bar heat sealer or heated wire in a desired shape, to seal and trim the bag 108, as seen in FIG. 4C, along a front seam 108*e* and the closed end 108*d*, and excess material may be trimmed from the open end 108*c* of the bag 108.

Figure 6:
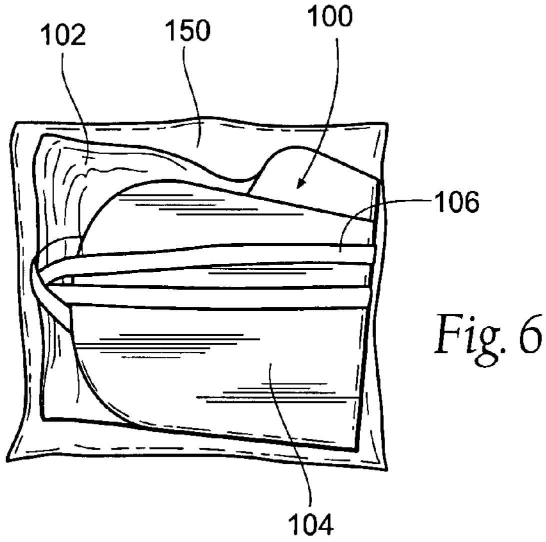
FIG. 6 is a top plan view of the embodiment of FIG. 1 in a folded and packaged configuration.

An emesis container according to the present invention is preferably packaged in a compact way that allows easy deployment by users in emergency medical situations, among others. The ease in deployment is facilitated by convenient packaging 150. As seen in FIG. 6, an emesis container 100 is folded in such a way to allow compact packaging. The folding may be aided by the scoring or creases 146 provided in the chute 104. The package 150 is preferably formed from a plastic sheet material as is well known. An emesis container 100 in a packaged configuration is preferably no larger than four inches long by four inches wide by one-half of an inch thick. Such a size enables convenient, easy storage of the devices.

While the emesis container was designed to be rather self-explanatory to use, the packaging 150 may further contain instructions (not shown) directed to proper use of the container 100, adjustment of the retainer 106, and proper disposal methods.

Figure 7:
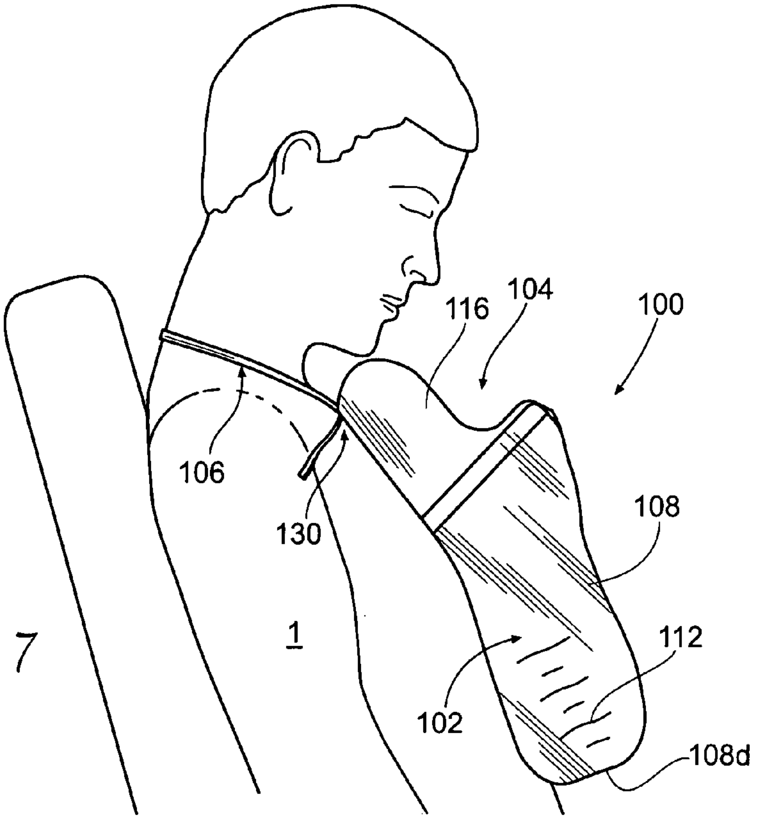
FIG. 7 is a left side elevation view of the embodiment of FIG. 1 in use.
Figure 8:
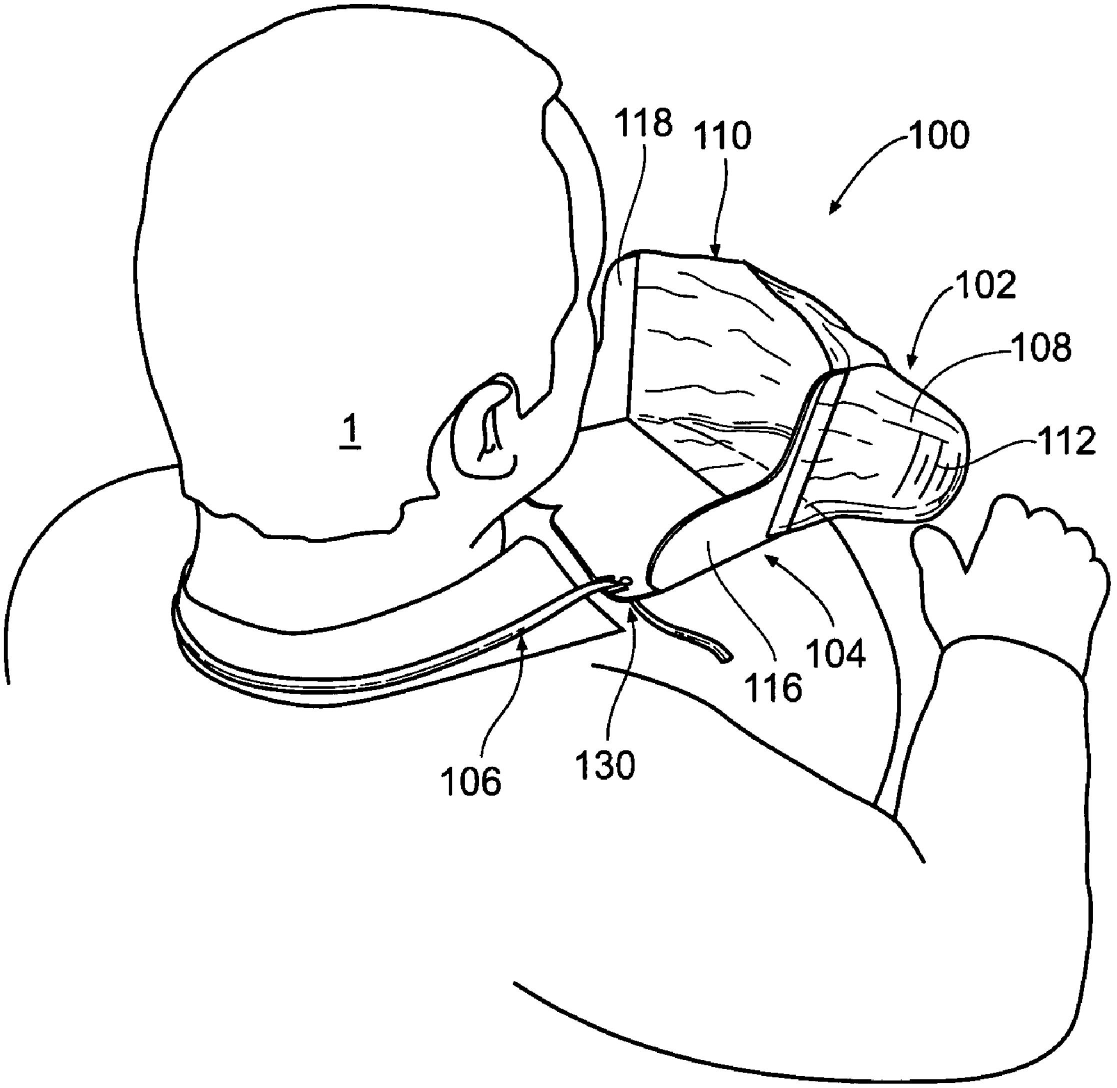
FIG. 8 is a top perspective view of the embodiment of FIG. 1 in use.

With reference to FIGS. 7 and 8, to use an emesis container according to the present invention, a user removes a container 100 from its package 150, unfolds the container 100, and places the retainer 106 about a support structure, such as the neck of the patient 1, to allow positioning of the chute 104 under the chin of the patient 1. The retainer 106 maintains proximity between the emesis container 100 and the mouth of the patient 1. Preferably, the patient 1 may be positioned in various poses and the retainer 106 will maintain such proximity, such as when the patient 1 is walking, standing, or sitting, or when the patient 1 is in a semi-Fowler's, a high-Fowler's, a left-lateral, or a right-lateral position. Indeed, the container 100 may even be used when the patient 1 is fitted with a cervical brace.

The retainer 106 is adjusted to provide proper positioning. Where the retainer 106 is a flat strap 132, the strap 132 may be adjusted a number of ways. While the strap 132 could be provided with an adjustment buckle, preferred adjustment is achieved by using the retainer site 130. If the strap 132 is kept in frictional contact with the chute 104 by a staple 144, the strap 132 may be pulled through the staple 144 to adjust positioning of the container 100.

A staple 144 may not work for some situations, however. For example, the retainer 106 may not be long enough to easily slip over a desired support structure. In such circumstances, the retainer 106 is preferably a flat strap 132 in cooperation with the chute 104 at a retainer site 130 having an aperture 134. The strap 132 can be removed from the site 130, threaded about a support member such as the neck of the patient 1, and threaded back through a hole 136 of the aperture 134 from which it was removed. While the strap 132 is in the hole 136, the strap 132 can move relatively freely through the aperture 134, thereby allowing easy adjustment. When desired positioning is achieved, the strap 132 can be forced into the slot 138 of the aperture 134. While the strap 132 is in the slot 138, a friction fit is provided, thereby maintaining the desired positioning.

To remove the container 100 from the patient 1, one method involves lifting or supporting the container 100 while removing the retainer 106 from the support structure. For instance, if the retainer 106 is a strap 132, the strap 132 may be lifted up and over the patient's head. Alternatively, the retainer 106 may be disconnected from one or both retainer sites 130. If the retainer 106 is a strap 132 coupled to the chute 104 by a staple 144, the strap 132 may be pulled out of the friction fit and the container 100 removed from the patient 1. Alternatively, if a staple 144 is used, the retainer site 130 may be provided with the perforated section 148 to enable tearing or removal of a portion the chute material for a quick disconnect of the device 100 from a patient or other support upon the exertion of a determinable force. This method is preferred if the strap 132 includes an anti-slip mechanism, such as an aglet. In a similar fashion to using a strap 132 in combination with a staple 144, if the retainer 106 is a strap 132 in frictional cooperation with an aperture 134 at a retainer site 130, the strap 132 could be removed from the aperture 134; or the chute 104, itself, may be caused to fail at a stress riser 142 formed by the aperture 134 and cooperating notches 140. Once the container 100 is removed from the patient 1, the container 100 is simply disposed of, preferably by being thrown into a biohazard receptacle.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An emesis container comprising:

a. a receptacle having an open end and a closed end, said open end having a perimeter;

b. a chute having an entrance end and an exit end oppositely disposed the entrance end, the exit end being coupled to the receptacle proximate the open end at a coupling location, the chute extending around less than the entire perimeter, wherein the chute comprises b1. a back panel having a front surface and a back surface, the back panel extending between and including the entrance end and the exit end;

b2. two side panels extending away from the back panel front surface, the side panels extending between and including the entrance end and the exit end, the side panels having a first edge portion at the entrance end, a second edge portion directly coupled to the back panel, and a third edge portion disposed opposite the second edge portion, wherein the first edge portion and the third edge portion are non-collinear and the first edge portion connects the third edge portion to the second edge portion; and b3. an attachment margin extending towards the entrance end, from and including at least a portion of the exit end of the back panel and at least a portion of each of the side panels, wherein the attachment margin is directly coupled to the receptacle, wherein the back panel and side panels extend around less than the bag open end perimeter; and c. a retainer directly coupled to the chute at least one retainer site.

2. An emesis container according to claim 1, further comprising a reinforcement member coupled to the chute, the reinforcement member adapted to maintain the chute in a substantially open configuration when the container is arranged for use.

3. An emesis container according to claim 2, wherein the reinforcement member is coupled to the chute proximate the coupling location.

4. An emesis container according to claim 2, wherein the reinforcement member is a plastically deformable metal wire being shorter in length than the circumference of the receptacle open end perimeter.

5. An emesis container according to claim 1, wherein the receptacle comprises a flexible material.

6. An emesis container according to claim 5, wherein the flexible material comprises plastic.

7. An emesis container according to claim 6, wherein the plastic comprises polyethylene.

8. An emesis container according to claim 1, wherein the receptacle is translucent.

9. An emesis container according to claim 1, the receptacle further including volume demarcations.

10. An emesis container according to claim 1, the receptacle having a liquid capacity of at least 1200 milliliters.

11. An emesis container according to claim 10, the receptacle having a liquid capacity of 2500 milliliters.

12. An emesis container according to claim 1, wherein the chute comprises a chute material and the receptacle comprises a receptacle material, said chute material being more rigid than said receptacle material.

13. An emesis container according to claim 1, wherein the chute comprises paperboard having a liquid impervious coating on at least one surface.

14. An emesis container according to claim 1, wherein the retainer is a strap capable of forming a loop with the entrance end of the chute.

15. An emesis container according to claim 14, wherein the strap is elastic.

16. An emesis container according to claim 1, further comprising a stress riser formed in the chute and located proximate at least one of the at least one retainer site to enable decoupling of the at least one of the at least one retainer site from the chute.

17. An emesis container according to claim 1, wherein the retainer is a strap, and wherein at least one of the at least one retainer site comprises a fastener maintaining the strap in slidable frictional contact with the chute.

18. An emesis container according to claim 17, wherein the fastener is a staple that impenetrably surrounds a portion of the strap.

19. An emesis container according to claim 1, the chute side panels further comprising at least one support tab extending away from the back panel front surface, said at least one support tab being directly coupled to the chute and the receptacle along at least a portion of the coupling location and adapted to support at least a portion of the open end of the receptacle.

20. An emesis container according to claim 19, wherein the at least one support tab is formed integrally with at least a portion of the chute exit end.

21. An emesis container according to claim 1, wherein the open end perimeter encompasses at least thirty square inches.

22. An emesis container according to claim 1, wherein the attachment margin is a portion of the chute folded towards, and disposed at an angle with respect to, the chute back panel back surface, thereby forming a fold into which at least a portion of the receptacle is inserted, said angle being less than ninety degrees.

23. An emesis container according to claim 1, wherein the back panel front surface has an area of at least forty square inches.

* * * * *

UNITED STATES PATENT AND TRADEMARK OFFICE

CERTIFICATE OF CORRECTION

PATENT NO. : 7,686,791 B2
APPLICATION NO. : 11/714949
DATED : March 30, 2010
INVENTOR(S) : Richard F. Ramage et al.

It is certified that error appears in the above-identified patent and that said Letters Patent is hereby corrected as shown below:

Column 6, line 34, delete "non-collinear" and substitute -- non-colinear --

Column 6, line 44, after "the chute at" insert -- at -- to correctly read "the chute at at least one retainer site".

Signed and Sealed this

Eighteenth Day of May, 2010

David J. Kappos
*Director of the United States Patent and Trademark Office*